(12) United States Patent
Mitterer et al.

(10) Patent No.: US 9,701,710 B2
(45) Date of Patent: Jul. 11, 2017

(54) PROTEIN PURIFICATION BY ANION EXCHANGE CHROMATOGRAPHY

(71) Applicants: Baxalta Incorporated, Bannockburn, IL (US); Baxalta GmbH, Glattpark (Opfikon) (CH)

(72) Inventors: Artur Mitterer, Orth/Donau (AT); Meinhard Hasslacher, Vienna (AT); Christian Fiedler, Vienna (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 14/351,544

(22) PCT Filed: Oct. 12, 2012

(86) PCT No.: PCT/EP2012/070259
§ 371 (c)(1),
(2) Date: Apr. 11, 2014

(87) PCT Pub. No.: WO2013/053888
PCT Pub. Date: Apr. 18, 2013

(65) Prior Publication Data
US 2014/0302592 A1    Oct. 9, 2014

Related U.S. Application Data

(60) Provisional application No. 61/547,513, filed on Oct. 14, 2011.

(51) Int. Cl.
| | | |
|---|---|---|
| C07K 1/14 | (2006.01) | |
| C07K 1/18 | (2006.01) | |
| C12N 9/64 | (2006.01) | |
| C07K 14/47 | (2006.01) | |

(52) U.S. Cl.
CPC .............. *C07K 1/145* (2013.01); *C07K 1/18* (2013.01); *C07K 14/47* (2013.01); *C07K 14/473* (2013.01); *C07K 14/4721* (2013.01); *C12N 9/644* (2013.01); *C12N 9/6432* (2013.01); *C12N 9/6437* (2013.01); *C12Y 304/21021* (2013.01); *C12Y 304/21022* (2013.01)

(58) Field of Classification Search
CPC .................................................... C07K 1/145
See application file for complete search history.

(56) References Cited

U.S. PATENT DOCUMENTS

| | | | |
|---|---|---|---|
| 4,981,952 A * | 1/1991 | Yan | C07K 14/745 530/384 |
| 5,633,350 A | 5/1997 | Fischer | |
| 6,869,934 B2 * | 3/2005 | Mizokami | C07K 14/4721 530/350 |
| 2008/0207879 A1 | 8/2008 | Artur et al. | |
| 2009/0311239 A1 | 12/2009 | Chtourou et al. | |
| 2010/0047428 A1 | 2/2010 | Lejars et al. | |

FOREIGN PATENT DOCUMENTS

| | | | |
|---|---|---|---|
| EP | 0 363 126 A2 | 4/1990 | |
| WO | WO 96/40883 A1 | 12/1996 | |
| WO | WO 2006/035058 A2 | 4/2006 | |
| WO | WO 2006/067230 A1 * | 6/2006 | ............... C07K 1/16 |
| WO | WO 2007/026020 A1 | 3/2007 | |
| WO | WO 2011/073235 A1 | 6/2011 | |
| WO | WO 2011/135071 A1 | 11/2011 | |
| WO | WO 2013/053887 A1 | 4/2013 | |
| WO | WO 2013/053888 A1 | 4/2013 | |

OTHER PUBLICATIONS

International Search Report mailed Nov. 13, 2012, for International Patent Application No. PCT/EP2012/070259, 5 pages.
Josic, D. et al., "Preparation of vitamin K-dependent proteins, such as clotting factors II, VII, IX and X and clotting inhibitor Protein C," *Journal of Chromatography B*, 2003, vol. 790, pp. 183-197.
Burger, A. et al., "A rapid and efficient purification method for recombinant annexin V for biophysical studies," FEBS, Aug. 1993, vol. 329, No. 1,2, pp. 25-28.
Kelley, B.D. et al., "Robustness Testing of a Chromatographic Purification Step Used in Recombinant Factor IX Manufacture," Chapter 8 in *ACS Symposium Series*, 1998, vol. 698, pp. 93-113.
Osborn, E.C., "The Employment of Deae-Cellulose Columns on a 'Rejection' Principle in the Preparation of Factor VII," Clinica Chimica Acta, 1965, vol. 12, pp. 415-418.

* cited by examiner

*Primary Examiner* — Amber D Steele
(74) *Attorney, Agent, or Firm* — Morgan, Lewis & Bockius LLP

(57) ABSTRACT

The present invention relates to a two-step method for the purification of divalent cation binding proteins with high yield and high purity on anion exchange resin materials, to divalent cation binding proteins obtainable by said method, and to a kit comprising means for carrying out said method.

17 Claims, No Drawings

PROTEIN PURIFICATION BY ANION EXCHANGE CHROMATOGRAPHY

This application is a U.S. National Phase application of International Patent Application No. PCT/EP2012/070259, filed Oct. 12, 2012, which claims the benefit of U.S. Provisional Patent Application No. 61/547,513, filed Oct. 14, 2011, Both hereby incorporated herein by reference in their entireties.

FIELD OF THE INVENTION

The present invention relates to a two-step method for the purification of divalent cation binding proteins with high yield and high purity on anion exchange resin materials, to divalent cation binding proteins obtainable by said method, and to a kit comprising means for carrying out said method.

BACKGROUND OF THE INVENTION

So far, many mammalian proteins are produced in host cells by e.g. transfecting cells with DNA encoding said proteins and growing the recombinant cells under conditions favourable for the expression of said proteins. The proteins secreted by the cells into the cell culture medium, or residing inside the cells, can be separated from the culture medium and other components using chromatographic techniques, e.g. ion exchange chromatography, affinity chromatography, and the like. For further pharmaceutical applications, purity is of particular importance. However, at the same time the biological activity of the protein must be preserved after thorough purification of the proteins of interest.

The concept of eluting calcium binding proteins from anion exchange resins by divalent cations was firstly reported almost thirty years ago. Although bovine Factor VII was successfully isolated from bovine plasma, the purification of human Factor VII was still problematic, i.e. the material produced was only partially pure or was obtained in such small quantities that it was characterized as activity without detectable protein. Workers in the field succeeded in the isolation of human Factor VII from human plasma in sufficient quantities (with a yield of approx. 30%) by means of adsorbing proteins to a divalent cation, i.e. barium citrate, and then separating the protein by anion exchange chromatography. Further, methods were available for recovering and purifying vitamin K-dependent proteins from the medium of a cell culture producing vitamin K-dependent proteins with different specific activities by Means of conventional ion-exchange resins, e.g. anion exchange resins, and using an eluant containing divalent cations, e.g. calcium ion ($Ca^{2+}$), barium ion ($Ba^{2+}$), and strontium ion ($Sr^{2+}$).

Furthermore, methods were available for the purification of Factor IX (FIX) in a solution, comprising the steps of applying the solution containing FIX to an anion exchange resin, washing the anion exchange resin with a solution having a conductivity that is less than required to elute FIX from the resin, and eluting FIX from the anion exchange resin with a first eluant including divalent cations to form a first eluate. The first eluate is then applied to a heparin or heparin-like resin to form a second eluate, and the second eluate is applied to hydroxyapatite to form a third eluate, utilizing a high conductivity washing agent in the washing step.

Factor IX (FIX) is a vitamin K-dependent serine protease of the coagulation system, belonging to the peptidase family S1. FIX is inactive unless activated by Factor XIa or Factor VIIa. For its activation, calcium, and membrane phospholipids are required. Deficiency of FIX causes the hereditary recessive bleeding disorder hemophilia B, which can be successfully treated by administration of posttranslational modified, i.e. phosphorylated and sulfated FIX.

Further, Factor VII (FVII) is a vitamin K-dependent serine protease which plays a significant role in the coagulation cascade, where it initiates the process of coagulation with tissue factor (TF). Upon vessel injury, TF is exposed to the blood and circulating FVII. Once bound to TF, FVII is activated to FVIIa by thrombin, Factor Xa, IXa, XIIa, and the FVIIa-TF complex whose substrates are FX and FIX. Furthermore, Annexin V is a cellular protein in the annexin group, having the ability to bind in a calcium-dependent manner to phosphatidylserine and to form a membrane-bound two dimensional crystal lattice. It may play a role in blood coagulation, apoptosis, phagocytosis and formation of plasma membrane-derived microparticles.

Thus, the problem underlying the present invention is to provide an improved method for the purification of divalent cation binding proteins with high yield and high purity. The solution to the above technical problem is achieved by the embodiments characterized in the claims.

SUMMARY OF THE INVENTION

The present invention relates to a method for the purification of a divalent cation binding protein comprising the steps of:

(a) loading a first anion exchange resin material with the divalent cation binding protein in a loading buffer in the absence of divalent cations, and optionally washing the loaded anion exchange resin material with a washing buffer in the absence of divalent cations;

(b) eluting the divalent cation binding protein with an eluant comprising a counter-anion to form an eluate containing the divalent cation binding protein;

(c) supplementing the eluate obtained in step (b) with at least one divalent cation and increasing the pH;

(d) loading a second anion exchange resin material with the supplemented eluate obtained in step (c); and (e) collecting the flow-through containing the divalent cation binding protein.

2. The method according to item 1, wherein in step (c) the pH of the supplemented eluate is increased by at least 0.5 pH units.

3. The method according to item 1 or 2, wherein the eluant in step (b) has a conductivity that is higher than the conductivity of the loading buffer in step (a) and the washing buffer in step (a), in case a washing step is carried out, and wherein the supplemented eluate in step (c) has a conductivity that is lower than the conductivity of the eluant in step (b).

4. The method according to any of items 1 to 3, wherein the at least one divalent cation in step (c) is selected from the group consisting of $Ca^{2+}$, $Be^{2+}$, $Ba^{2+}$, $Mg^{2+}$, $Mn^{2+}$, $Sr^{2+}$, $Zn^{2+}$, $Co^{2+}$, $Ni^{2+}$, and $Cu^{2+}$, or combinations thereof.

5. The method according to anyone of items 1 to 4, wherein the first and second anion exchange resin materials each have a positively charged group which is independently selected from the group, consisting of diethylaminoethane (DEAE), dimethylaminoethane (DMAE), trimethylaminoethyl (TMAE), polyethyleneimine (PEI), quaternary aminoalkyl, quaternary aminoethane (QAE), and quaternary ammonium (Q).

6. The method according to anyone of items 1 to 5, wherein the first and second anion exchange resin materials each carry a primary amine as ligand which is independently selected from the group, consisting of aminohexyl, benzamidine, lysine, and arginine.
7. The method according to anyone of items 1 to 6, wherein the divalent cation binding protein is a calcium binding protein.
8. The method according to anyone of items 1 to 7, wherein the divalent cation binding protein is a vitamin K-dependent protein.
9. The method according to anyone of items 1 to 8, wherein the divalent cation binding protein is selected from the group, consisting of Factor II, Factor VII, Factor IX, Factor X, Protein C, Protein S, Annexin and calmodulin, particularly preferred from the group consisting of Factor IX, Factor VII, and Annexin V.
  The divalent cation binding protein can be either derived from a natural source, e.g. plasma, or can be recombinantly produced.
10. The method according to any one of items 1 to 9, wherein the pH of the loading buffer in the loading step (a) and/or the pH of the wash buffer in the optional wash step (a) is ≤pH 7.4, preferably between pH 5.5 and pH 7.0, even more preferred between pH 6.0 and pH 7.0, even more preferred between pH 6.5 and pH 7.0.
11. A purified divalent cation binding protein obtainable by a method according any one of items 1 to 10.
12. A kit comprising means for carrying out the method according to any one of items 1 to 10.

Thus, the present invention also relates to purified divalent cation binding proteins obtainable by the above method, and to a kit comprising means for carrying out the above method.

DETAILED DESCRIPTION OF THE INVENTION

In one aspect, the present invention relates to method for the purification of a divalent cation binding protein comprising the steps of:
(a) loading a first anion exchange resin material with the divalent cation binding protein in a loading buffer in the absence of divalent cations or at a low concentration thereof, and optionally washing the loaded anion exchange resin material with a washing buffer in the absence of divalent cations;
(b) eluting the divalent cation binding protein with an eluant comprising a counter-anion to form an eluate containing the divalent cation binding protein;
(c) supplementing the eluate obtained in step (b) with least one divalent cation and increasing the pH;
(d) loading a second anion exchange resin material with the supplemented eluate obtained in step (c); and
(e) collecting the flow-through containing the divalent cation binding protein.

The term "in the absence of divalent cations" as used herein refers to the absence of free divalent cations in the buffer, wherein divalent cations that are bound to a protein or complexed with or by a chelator, e.g. EDTA, may be present. "at a low concentration thereof" in this context refers to a divalent cation concentration in the µM range, in particular a concentration of 1000 µM at most, preferably 800 µM at most, even more preferred 500 µM at most. For this application the term "in the absence of divalent cations" is meant to also encompass the above definition for "at a low concentration thereof".

Loading of the first anion exchange resin material with the divalent cation binding protein in a loading buffer in the absence of divalent cations can be carried out by any method known in the art. In particular, conditions suitable for loading the divalent cation binding protein to the anion exchange resin material are well known to a person skilled in the art. The specific conditions for the conductivity of the loading buffer that allows binding of the product depend on the particular properties of the protein and the anion exchange resin material used (e.g. ligand density, ligand presentation, etc.). Divalent cations bind to proteins in regions that are usually highly acidic (i.e. negatively charged). The negative charges are masked when the divalent cation is bound. However, by loading the anion exchange material with the divalent cation binding protein in the absence of divalent cations, e.g. by stripping off the bound divalent cation by a chelator, e.g. EDTA, the protein carries highly negatively charged patches on the surface that allow strong binding to an anion exchange ligand. The conditions for loading a protein onto an anion exchange resin material further always require a balance between pH and the concentration of the counterions, e.g. $Cl^-$. The chemistry of the counter-ion also influences the elution behavior, e.g. $Cl^-$ carries one negative charge, and phosphate at neutral pH carries two negative charges. The latter can have a higher eluting power compared to $Cl^-$, even when the conductivity is lower.

The salt concentrations of the solutions and buffers used in the present invention are typically in the range between 20 and 200 mM (NaCl), preferably between 100 and 150 mM (NaCl) for the wash buffer. The preferred salt concentrations for the elution buffer are 300-400 mM (NaCl) while the column equilibration buffers will preferably have the same conductivity and/or NaCl concentration as the load.

Further, suitable loading buffers for loading a divalent cation binding protein to an anion exchange material in step (a) of the method of the present invention, providing conditions under which the divalent cation binding protein is bound to the anion exchange material are well known in the art. For example, the loading buffer can have a pH of ≤pH 7.4, preferably ≤pH 7.0, more preferably ≤pH 6.5, and most preferably ≤pH 6.0. Preferably, the ≤pH of the loading buffer is not lower than 5.5, preferably between pH 5.5 and pH 7.0, even more preferred between pH 6.0 and pH 7.0, even more preferred between pH 6.5 and pH 7.0.

The load can be e.g. a cell culture supernatant comprising the divalent cation binding protein and being essentially carbonate-buffered, with or without an additional loading buffer.

The loading buffer for the second anion exchange step can be the same as above for the first anion exchange step. The difference between the two anion exchange steps as provided according to the present invention is essentially the following:
  a) The first anion exchange column is loaded with the starting material, i.e. in a preferred embodiment with the cell culture material. This is a highly impure starting material. The second anion exchange column is loaded with material which has already been purified to some extent, as it is the material obtained after the elution (and supplementation) step.
  b) The first anion exchange step is carried out in the absence of divalent cations, while when carrying out the second anion exchange step, the load material has been supplemented with divalent cations.
  c) The conductivity of the load on the second anion exchange is selected in a preferred embodiment so as to be lower than the conductivity of the elution step on the first anion exchange column.

d) Consequently, the first anion exchange step is carried out in a product-binding mode while the second anion exchange step is carried out in a product-non-binding mode.

It may contain any salt concentrations suitable for binding the divalent cation binding protein to the anion exchange resin material which may be easily determined by a person skilled in the art. In a preferred embodiment, the loading buffer may contain a chelating agent, e.g. EDTA, preferably 2 mM EDTA. A loading buffer containing the divalent cation binding protein which may be applied to the anion exchange resin material in the method of the present invention may contain for example 20 mM MES and 2 mM EDTA.

The method of the present invention optionally comprises the step of washing the loaded anion exchange resin material with a washing buffer in the absence of divalent cations. This washing step can be carried out by any method known in the art. Suitable washing buffers for washing impurities off the anion exchange material essentially without eluting the divalent cation binding protein are well known in the art. For example, the washing buffer can have a pH ≤pH 7.4, preferably ≤pH 7.0, more preferably ≤pH 6.5, and most preferably ≤pH 6.0. Preferably, the pH is not lower than 5.5, preferably between pH 5.5 and pH 7.0, even more preferred between pH 6.0 and pH 7.0, even more preferred between pH 6.5 and pH 7.0.

It may contain any salt concentrations suitable for washing the anion exchange resin material without eluting the divalent cation binding protein in a significant amount which. may be easily determined by a person skilled in the art. For example, the washing buffer may contain a suitable buffer agent like for example Tris or MES, preferably 20 mM MES. Additionally, it may contain a chelating agent like for example EDTA, preferably 2 mM EDTA. Further, it may contain a suitable salt for regulating the conductivity of the washing buffer, like for example NaCl, which may be present in a concentration of ≤200 mM, preferably from 100 mM to 200 mM, more preferably from 150 mM to 200 mM, more preferably from 170 mM to 190 mM, and most preferably from 175 mM to 185 mM. In another preferred embodiment of the present application, the washing buffer contains 100 to 200 mM NaCl. The absolute value for the salt concentration depends on the divalent cation binding protein to be purified, wherein it is within the knowledge of the person skilled in the art to determine which divalent cation binding proteins require lower or higher salt concentrations to get the optimal purity.

Eluting the divalent cation binding protein with an eluant comprising a counter-ion can be carried out by any method known in the art. In particular, suitable eluants containing suitable counter-ions are well known in the art. Preferred counter-ions include Cl⁻, bromide, borate, sulfonic acids and acetate, wherein Cl⁻ is particularly preferred. In a preferred embodiment, the pH of the eluant is the same as the pH of the loading buffer in step (a). For example, the eluant can have a pH ≤pH 7.4, preferably ≤pH 7.0, more preferably ≤pH 6.5, and most preferably ≤pH 6.0, preferably not lower than pH 5.5, preferably between pH 5.5 and pH 7.0, even more preferred between pH 6.0 and pH 7.0, even more preferred between pH 6.5 and pH 7.0.

It may contain any salt concentrations suitable for eluting the divalent cation binding protein from the first anion exchange resin material without eluting impurities in a significant amount which may be easily determined by a person skilled in the art. For example, it may contain a suitable buffer agent like for example MES, preferably 20 mM MES, Tris, HEPES, Tris/acetate, histidine, Gly-Gly, MOPS, or tricine, at concentrations ranging typically from 5 to 50 mM. The following is a list of particularly preferred buffers:

Tris: (buffers at pH=8.06±1.0)
MES: (buffers at pH=6.2±1.0)
HEPES: (buffers at pH 7.7±1.0)
MOPS: (buffers at pH=7.3±1.0)
Tricine: (buffers at pH=8.3±1.0)
Histidine: (buffers at pH=7.6±1.0)
Gly-Gly: (buffers at pH=7.4±1.0)
Bis-Tris: (buffers at pH=6.35±1.0)
ACES: (buffers at pH=7.0±1.0) (N-(2-Acetamido)-2 aminoethanesulfonic acid)
ADA: (buffers at pH=7.0±1.0) (N-(2-Acetamido)-iminodiacetic acid) It may also contain a suitable salt for regulating the conductivity of the washing buffer, like for example NaCl, which may be present in a concentration of 100-200 mM. The absolute value for the salt concentration depends on the divalent cation binding protein to be purified, wherein it is within the knowledge of the person skilled in the art to determine which divalent cation binding proteins require lower or higher salt concentrations to get the optimal purity. An eluant which may be applied in the method of the present invention may contain for example 20 mM MES and 350 mM NaCl and may have a pH of 6.0.

According to the method of the present invention, the eluate obtained in step (b) is supplemented with at least one divalent cation in step (c). In a preferred embodiment, the eluate is supplemented with a divalent cation, selected from the group consisting of $Ca^{2+}$, $Be^{2+}$, $Ba^{2+}$, $Mg^{2+}$, $Mn^{2+}$, $Sr^{2+}$, $Zn^{2+}$, $Co^{2+}$, $Ni^{2+}$, and $Cu^{2+}$, or combinations thereof. The cation is preferably present in the supplemented eluate in a concentration from 1 mM to 20 mM, more preferably in a concentration from 1 mM to 10 mM, most preferably in a concentration of 2 mM. The cation is present in the eluate in the form of a suitable salt with an anion. Suitable anions are known to a person skilled in the art and comprise for example sulfate-, phosphate-, carbonate-, and borate-based anions, or combinations thereof. The salt comprising the divalent cation may be present in the eluate in a concentration from 1 mM to 20 mM, preferably 2 mM. In a preferred embodiment, the salt is $CaCl_2$. In a particularly preferred embodiment, the eluate contains 2 mM $CaCl_2$.

According to the method of the present invention, the pH in the supplemented eluate obtained in step (b) is increased in step (c). In preferred embodiments, the pH of the supplemented eluate is increased by at least 0.5 pH units, preferably at least 1.0 pH units, more preferably at least 1.5 pH units, most preferably at least 2.0 pH units. Preferably, the supplemented eluate has a pH of more than 6.5, preferably of more than 7.0, even more preferred a pH ≥7.4, and more preferably ≥8.0, but not more than pH 9.0, provided the pH of the supplemented eluate in step (c) is higher than the pH of the eluant in step (b).

In preferred embodiments of the method of the present invention, the eluant in step (b) has a conductivity that is higher than the conductivity of the loading buffer in step (a) and, in case a washing step is carried out, the washing buffer in step (a), and the supplemented eluate in step (c) has a conductivity that is lower than the conductivity of the eluant in step (b). In particular, the loading buffer in step (a) and, in case a washing step is carried out, the washing buffer in step (a) may have a conductivity of 8-18 mS/cm (room temperature). Further, the elution buffer in step (b) may have a conductivity of 25-35 mS/cm (room temperature). Finally, the supplemented eluate in step (c) may have a conductivity of c: <18 mS/cm (room temperature).

As used herein, the term "anion exchange resin material" does not underlie a specific restriction. According to the present invention, the first and second resin includes any material suitable for anion exchange chromatography known in the art, like for example an agarose based chromatography material, e.g. sepharoses like Fast Flow or Capto, polymeric synthetic material, e.g. polymethacrylate like Toyopearls, polystyrene/divinylbenzene, e.g. Poros, Source, or cellulose. In a specific example of the present invention, the first and second anion exchange resin material is sepharose, which is based on modified agarose, the polysaccharide chains of which are crosslinked to form a three-dimensional network. In a preferred embodiment, the first and second anion exchange resin materials include, but are not limited to resins that carry a primary amine as ligand, e.g. aminohexyl sepharose, benzamidine sepharose, lysine sepharose, or arginine sepharose. In another preferred embodiment, the first and second anion exchange resin materials include, but are not limited to resins having a positively charged moiety at neutral pH, such as alkylaminoethane, like diethylaminoethane (DEAE), dimethylaminoethane (DMAE), or trimethylaminoethyl (TMAE), polyethyleneimine (PEI), quaternary aminoalkyl, quaternary aminoethane (QAE), quaternary ammonium (Q), and the like. In a particularly preferred embodiment the anion exchange resin material is Q-Sepharose Fast Flow (Q-Sepharose FF). According to the method of the present invention, the first and second anion exchange resin materials may be the same or may be different.

The divalent cation binding protein according to the present invention may be any divalent cation binding protein, like for example a calcium binding protein and/or a vitamin K-dependent protein. In a preferred embodiment, the divalent cation binding protein is selected from the group, consisting of factor II, factor VII, factor IX, factor X, Protein C, Protein S, Annexin and calmodulin, particularly preferred from the group consisting of factor IX (FIX), factor VII (FVII), and Annexin V.

The divalent cation binding protein may be obtained using methods known to a person skilled in the art like, e.g. plasma derived proteins, transgenically produced proteins, or recombinantly produced proteins, for example using CHO cells. Secretory and non-secretory methods for extracting proteins from cell culture are well known to a person skilled in the art. This may include any method known in the art for (i) the production of recombinant DNA by genetic engineering, e.g. via reverse transcription of RNA and/or amplification of DNA, (ii) the introduction of recombinant DNA into prokaryotic or eukaryotic cells by transfection, e.g. via electroporation or microinjection, (iii) the cultivation of said transformed cells, e.g. in a continuous or batchwise manner, (iv) the expression of a divalent cation binding protein, e.g. constitutive or upon induction, and (v) the isolation of the protein, e.g. from the culture medium or by harvesting the transformed cells, in order to obtain a crude divalent cation binding protein. Additionally, the recombinant DNA encoding a divalent cation binding protein, e.g. a plasmid, may also contain a DNA sequence encoding a selectable marker for selecting the cells which have been successfully transfected with the recombinant DNA.

The proteins may be pre-purified to reduce impurities, for example by gel electrophoresis, chromatography, gel filtration, centrifugation, filtration, precipitation, crystallization or any other method known in the art. The term "impurity" as used herein includes any impurity originating from the production of the divalent cation binding protein and may include e.g. host cell protein (HOP) impurities, nucleic acid impurities, polypeptide impurities, buffer and salt impurities, impurities originating from the cell culture medium, product related impurities, such as dimers or fragments, and combinations thereof.

In a preferred embodiment, the divalent cation binding protein which has been purified according to the method of the present invention has a purity with respect to host cell protein impurities of at least 95% w/w, more preferably at least 98% w/w, more preferably at least 99% w/w, and most preferably at least 99.5% w/w divalent cation binding protein in total protein. Accordingly, in a preferred embodiment, the content of impurities in the purified divalent cation binding protein is less than 5% w/w, more preferably less than 2% w/w, more preferably less than 1% w/w, and most preferably less than 0.5% w/w. The percentage values of the impurities refer to w/w of product, i.e. the purified divalent cation binding protein, and can be measured, for example, by HPLC or ELISA.

Further, in another aspect of the present invention, a purified divalent cation binding protein is provided which is obtainable by the method of the present invention, as well as a kit comprising means for carrying out the method of the present invention. In particular, the kit of the present invention may contain a loading buffer and/or an eluant and/or a washing buffer and/or a solution of divalent cations which are suitable for the purification of a divalent cation binding protein using an anion exchange resin material according to the present invention. In a preferred embodiment, the loading buffer, the washing buffer and/or the eluant are as defined above. Further, the kit of the present invention may contain a suitable anion exchange resin material.

The present invention further relates to the use of the method of the present invention as defined above and/or of the kit of the present invention as defined above for the purification of a divalent cation binding protein.

The present invention provides an efficient method for the purification of a divalent cation binding protein using anion exchange resin materials allowing a high reduction of process related impurities of the protein with concomitantly high product yields.

In particular, the method of the present invention is based on the following principles. Generally, binding of proteins to anion exchange resin materials is increased at lower conductivities and higher pH values. Vice versa, binding of proteins to anion exchange resin materials is decreased at higher conductivities and lower pH values. In the method of the present invention, the divalent cation binding protein is preferably loaded and/or washed at a low pH which still allows binding of the divalent cation binding protein to the first anion exchange material and does not harm the structural integrity or the activity of the divalent cation binding protein. At such conditions, many protein impurities, in particular those having a higher isoelectric point (pI) than the divalent cation binding proteins, do not bind to the first anion exchange resin material, and, therefore, binding of impurities to the first anion exchange resin material is greatly reduced. Protein impurities that do bind to the first anion exchange resin material under these conditions, i.e. protein impurities having a low pI, may co-elute with the divalent cation binding protein during elution. However, the increase of the pH in the supplemented eluate causes all proteins to bind even stronger to the second anion exchange resin material. According to the method of the present invention, only the divalent cation binding protein does not bind to the second anion exchange material due to the divalent cations present in the supplemented eluate. In this context, it should be noted that increasing the pH before loading of an anion exchange resin material is very atypical for a negative chromatography, i.e. a chromatography wherein the protein to be purified is expected in the flow-through, since, as has been stated above, proteins generally bind stronger to anion exchange resin materials at higher pH values. By supplementing the eluate from the first anion exchange resin material with at least one divalent cation, the method of the present invention surprisingly and advantageously achieves superior purities of the divalent cation binding protein product by anion exchange chromatography.

In particular, the present invention advantageously modifies the surface charge of the proteins to be purified by increasing the pH before loading of the second anion exchange resin material. An increased pH for loading the second anion exchange resin material forces impurities to bind to the second anion exchange resin material while binding of the protein to be purified is inhibited by supplementing divalent cations. According to the present invention, the above conditions result in a high purity as well as high yields of divalent cation binding proteins. The method of the present invention may provide a significant reduction of process related polypeptide impurities e.g. by loading the protein solution onto an anion exchange resin material at reduced pH, eluting the product, supplementing the eluate with at least one divalent cation and increasing the pH, before loading the supplemented eluate onto a second anion exchange resin material, and collecting the flow-through.

Various modifications and variations of the described method and products of the invention will be apparent to those skilled in the art without departing from the scope and spirit of the invention. Although the invention has been described in connection with specific preferred embodiments, it should not be unduly limited to such embodiments.

Examples

The following examples are provided as a guide for a person skilled in the art. The examples should not be construed as limiting the invention, the examples merely provide specific methodology useful in understanding and practising an embodiment of the invention.

Example 1

Purification of Recombinant (rFIX)

rFIX, a vitamin K-dependent protein, was produced by fermenting a genetically modified CHO cell line in a chemically defined media in chemostat mode. The product containing cell culture supernatant was clarified by depth filtration and filtration through a 0.2 µm filter. The clarified harvest was then supplemented with 2 mM EDTA and the pH was adjusted to 6.0 with a MES containing buffer. The rFIX contained in this clarified and conditioned harvest was then purified via a two-step chromatographic purification procedure on Q-Sepharose Fast Flow.

First Purification on Q-Sepharose Fast Flow (Ion Exchange Mode, pH=6.0)
The resin was first equilibrated with equilibration buffer (20 mM MES, 2 mM EDTA, pH=6.0) and then the conditioned rFIX containing load was applied to the resin. After a wash with wash buffer (20 mM MES, 2 mM EDTA, 180 mM NaCl, pH=6.0) the product was eluted with elution buffer (20 mM MES, 350 mM NaCl, pH=6.0). A summary of the product yields and impurity removal rates is shown in Table 1 with a typical performance of an Ion Exchange Capture step.

TABLE 1

First anion exchange purification on Q-Sepharose Fast Flow (Ion Exchange mode): Yield and purity

| Step | rFIX yield | | rFIX activity | | spec. activity | CHO HCP | |
|---|---|---|---|---|---|---|---|
| | mg | Yield % | Units | Yield % | Units/mg | mg | reduction |
| Load | 6.8 | — | 444 | — | 65 | 7.5 | — |
| Wash | 1.2 | 17 | 0.4 | 0.1 | <1 | 0.51 | — |
| Elution | 5.5 | 80 | 504 | 114 | 92 | 0.8 | 9.4 |

Second Purification on Q-Sepharose Fast Flow (Calcium Filtration Mode, pH=7.6)
The eluate pool obtained from the first purification step on Q-Sepharose Fast Flow was supplemented with approximately 8 mM $Ca^{2+}$, diluted with a Tris buffer to a conductivity of approximately 12 mS/cm (at room temperature) and the pH was set to 7.6. The resin was first equilibrated with equilibration buffer (20 mM Tris, 10 mM $CaCl_2$, 90 mM NaCl, pH=7.8) and the conditioned product containing solution was pumped over the column. The chromatographic conditions were set in a way that the product cannot bind whereas the majority of the CHO host cell protein impurities and inactive product species do bind to the anion exchange resin. The highly active and purified product is contained in the column flow through fraction of the second anion exchange step on Q-Sepharose Fast Fast Flow. Bound impurities are stripped from the resin with 1M NaCl. A summary of the product yields and impurity removal rates is depicted in Table 2.

TABLE 2

Second anion exchange purification on Q-Sepharose Fast Flow (Ca-filtration mode): Yield and purity

| Step | rFIX yield | | rFIX activity | | spec. activity | CHO HCP | |
|---|---|---|---|---|---|---|---|
| | mg | Yield % | Units | Yield % | Units/mg | mg | reduction |
| Load | 3.9 | — | 183 | — | 47 | 0.44 | — |
| Flow through | 1.4 | 35 | 241 | 132 | 175 | 0.011 | 40 |
| Elution | 2.4 | 60 | 441 | 23 | 18 | 0.54 | — |

The results show that the product contained in the non-binding fraction has a purity of >99% and a specific activity of 175 Units/mg. These data indicate that the second Anion Exchange purification step operated in Ca-filtration mode (non-product binding) at pH=7.6 has a significant removal capacity for the removal of process related impurities (CHO HOP) and product related impurities (inactive rFIX species) with a CHO reduction factor of 40 and an increase of the FIX specific activity by nearly 4-fold.

The combination of both chromatographic steps, the first anion exchange purification step at pH=6.0 (ion exchange mode) and the second anion exchange purification step (calcium filtration mode, non-product binding, pH=7.6) results in a CHO HCP removal rate of 376 which usually cannot be obtained with ion exchange chromatography. The purity of rFIX after the second anion exchange purification step (non-binding mode) is >99%.

Example 2

Purification of FVII with the 2-Step Ion Exchange Procedure on Poros Q rFVII, a Vitamin K-dependent protein was produced by fermenting a genetically modified CHO cell line in a chemically defined media in chemostat mode. The product containing cell culture supernatant was clarified by depth filtration and filtration through a 0.2 μm filter. The clarified harvest was then supplemented with 10 mM EDTA and the pH was adjusted to 6.0 with a MES containing buffer. The FVII contained in this clarified and conditioned harvest was then purified via a 2-step chromatographic purification procedure on Poros Q.

1) First Purification on Poros Q (Ion Exchange Mode, pH=6.0)

The resin was first activated with 8 column volumes of 1M NaCl to saturate the resin ligands with chloride. Then the resin was equilibrated with 8 column volumes equilibration buffer (20 mM MES, 2 mM EDTA, pH=6.0) followed by the loading of the conditioned FVII containing harvest at a linear flow rate of 60 cm/h. After loading was finished the column was washed with 5 column volumes of wash buffer 1 (20 mM MES, 2 mM EDTA, pH=6.0) and 10 column volumes of wash buffer (20 mM MES, 2 mM EDTA, 180 mM NaCl, pH=6.0). Bound FVII was eluted with 8 CV of elution buffer in ion-exchange mode (buffer: 20 mM MES, 2 mM EDTA, 350 mM NaCl, pH=6.0) at a linear flow rate of 30 cm/h. A summary of the product yields and impurity removal rates is shown in Table 3. About 96% of the CHO host cell protein was removed at this step resulting in a reduction factor of 23.

2) Second Purification on Poros Q (Calcium Filtration Mode, pH=>7.6, Room Temperature (RT)).

The eluate pool obtained from the first purification step on Poros Q was supplemented with approximately 8 mM $Ca^{2+}$, diluted with a Tris buffer to a conductivity of approximately 12 mS/cm (RT) and the pH was set to >7.6. (dilution buffer 1: 20 mM Tris, 10 mM $CaCl_2$, 0.1% Polysorbate 80, pH=7.8 RT, dilution buffer 2 (equilibration buffer): 20 mM Tris, 10 mM $CaCl_2$, 90 mM NaCl, 0.1% Polysorbate 80, pH=7.8 RT).

The resin was first equilibrated with 10 CV of equilibration buffer (20 mM Tris, 10 mM $CaCl_2$, 90 mM NaCl, 0.1% Polysorbate 80, pH=7.8 RT) and the calcium-supplemented FVII solution was pumped over the column. The chromatographic conditions were set in a way that the product did not bind whereas the majority of the CHO host cell protein impurities and inactive product species did bind to the Anion Exchange Poros Q resin. The active and purified product is contained in the column flow through fraction of the second Anion Exchange step on Poros Q. Bound impurities were stripped from the resin with 1M NaCl. A summary of the product yields and impurity removal rates is depicted in Table 4. The analytical data for the load fraction were taken from the eluate Pool of Ion Exchange run 1 (see Table 3). The results show that the product contained in the non-binding fraction has a purity of >95% and a specific activity of 3228 Units FVII/mg FVII Ag. These data indicate that the second Anion Exchange purification step operated in Ca-filtration mode (non-product binding) at >7.6 had a significant performance for the removal of process related impurities (CHO host cell proteins) with a CHO reduction factor of >27. About 99.9% of the CHO host cell protein was removed by the 2-step purification procedure resulting in a total CHO HCP reduction factor of >725.

SUMMARY

The combination of both chromatographic steps, i.e. the first Anion Exchange purification step at pH=6.0 (Ion Exchange mode) and the second Anion. Exchange purification step (Calcium filtration mode, non-product binding, pH=>7.6) on Poros Q, resulted in a CHO HCP removal rate of >725 which usually can only be obtained with Affinity but not with Ion Exchange Chromatography. The purity of rFVII after the second Anion exchange purification step (non-binding mode) was >95%. The data show that the 2-step purification method can also be applied and adapted for FVII (also a Vitamin-K dependent protein) and can be performed on an alternative Q-Resin.

TABLE 3

First Anion Exchange purification on Poros Q (Ion Exchange mode): Yield and impurity balance

| | FVII: Ag | | FVII: C | | CHO HCP | |
|---|---|---|---|---|---|---|
| Step | mg | Yield % | Units | Yield % | mg | reduction |
| Load | 5.93 | — | 17086 | — | 38.4 | — |
| Elution | 0.91 | 15 | 4414 | 26 | 1.68 | 23 |

The load, material was clarified cell culture supernatant of a FVII producing CHO cell line supplemented with 2 mM EDTA and pH-adjusted to 6.0. The purification experiment was performed with MES buffers at a pH6.0 and the elution was induced by chloride counter-ions. FV11:C: FVII chromogenic assay.

TABLE 4

Second Anion Exchange purification on Poros Q (Ca-filtration mode): Yield and impurity balance

| | FVII: Ag | | FVII: C | | CHO HCP | |
|---|---|---|---|---|---|---|
| Step | mg | Yield % | Units | Yield % | mg | reduction |
| Load | 0.91 | — | 4414 | — | 1.68 | — |
| Flow through | 1.04 | >100 | 3358 | 76 | <0.053 | >27 |
| Step 1 + 2 | | 17 | | 20 | | >725 |

The load material was the eluate pool of the first Anion Exchange purification step supplemented with 8 mM calcium and adjusted to pH=>7.6. The purification experiment was performed with Tris buffers at a pH>7.6 and the product was contained in the non-binding fraction.

FVII:C: FVII chromogenic assay.

Example 3

Purification of FVII with the 2-Step Ion Exchange Procedure on Q-Sepharose Fast Flow rFVII, a Vitamin K-dependent protein was produced by fermenting a genetically modified CHO cell line in a chemically defined media in chemostat mode. The product containing cell culture supernatant was clarified by depth filtration and filtration through a 0.2 μm filter. The clarified harvest was then supplemented with 10 mM EDTA and the pH was adjusted to 6.0 with a MES containing buffer. The FVII contained in this clarified and conditioned harvest was then purified via a 2-step chromatographic purification procedure on Q-Sepharose Fast Flow.

1) First Purification on Q-Sepharose Fast Flow (Ion Exchange Mode, pH=6.0)

The resin was first activated with 8 column volumes of 1M NaCl to saturate the resin ligands with chloride. Then the resin was equilibrated with 8 column volumes equilibration buffer (20 mM MES, 2 mM EDTA, pH=6.0) followed by the loading of the conditioned FVII containing harvest at a linear flow rate of 60 cm/h. After loading was finished the column was washed with 5 column volumes of wash buffer 1 (20 mM MES, 2 mM EDTA, pH=6.0) and 10 column volumes of wash buffer 2 (20 mM MES, 2 mM EDTA, 180 mM NaCl, pH=6.0). Bound FVII was eluted with 8 CV of elution buffer in ion-exchange mode (buffer: 20 mM MES, 2 mM EDTA, 350 mM NaCl, pH=6.0) at a linear flow rate of 30 cm/h. A summary of the product yields and impurity removal rates is shown in Table 5 with yields for FVII antigen and activity in the range of 63-67%. About 87% of the host cell protein was removed resulting in a reduction factor of 7.8.

2) Second Purification on Poros Q (Calcium Filtration Mode, pH=>7.6 RT)

The eluate pool obtained from the first purification step on Q-Sepharose Fast Flow was supplemented with approximately 8 mM Ca²⁺, diluted with a Tris buffer to a conductivity of approximately 12 mS/cm (RT) and the pH was set to >7.6. (dilution buffer 1:20 mM Tris, 10 mM CaCl$_2$, 0.1% Polysorbate 80, pH=7.8 RT, dilution buffer 2 (equilibration buffer): 20 mM Tris, 10 mM CaCl$_2$, 90 mM NaCl, 0.1% Polysorbate 80, pH=7.8 RT).

The resin was first equilibrated with 10 CV of equilibration buffer (20 mM Tris, 10 mM CaCl$_2$, 90 mM NaCl, 0.1% Polysorbate 80, pH=7.8 RT) and then the calcium-supplemented FVII solution was pumped over the column at a linear flow rate of 60 cm/h. The chromatographic conditions were set in a way that the product did not bind whereas the majority of the CHO host cell protein impurities did bind to the Anion Exchange Q-Sepharose Fast Flow resin. The active and purified product is contained in the column flow through fraction of the second Anion Exchange step on Q-Sepharose Fast Flow. Bound impurities were stripped from the resin with 1M NaCl. A summary of the product yields and impurity removal rates is depicted in Table 6. The analytical data for the load fraction were taken from the eluate Pool of Ion Exchange run 1 (see Table 5).

The results show that the product contained in the non-binding fraction has a purity of 99% and a specific activity of 2040 Units FVII/mg FVII Ag. These data indicate that the second Anion Exchange purification step operated in Ca-filtration mode (non-product binding) at pH=>7.6 had a significant performance for the removal of process related impurities (CHO host cell proteins) with a CHO reduction factor of 50. About 99.7% of the CHO host cell protein was removed by the 2-step purification procedure resulting in a total CHO HOP reduction factor of 395.

Summary Example 3

The combination of both chromatographic steps, i.e. the first Anion Exchange purification step at pH=6.0 (Ion Exchange mode) and the second Anion Exchange purification step (Calcium filtration mode, non-product binding, pH=>7.6) on Q-Sepharose Fast Flow, resulted in a CHO HCP removal rate of 395 which usually can only be obtained with Affinity but not with Ion Exchange Chromatography. The purity of rFVII after the second Anion exchange purification step (non-binding mode) was 99%. The data show that the 2-step purification method can also be applied and adapted for FVII.

TABLE 5

First Anion Exchange purification on Q-Sepharose Fast Flow (ion exchange mode): Yield and impurity balance

| | FVII: Ag | | FVII: C | | CHO HCP | |
|---|---|---|---|---|---|---|
| Step | mg | Yield % | Units | Yield % | mg | reduction |
| Load | 6.56 | — | 18375 | — | 22.5 | — |
| Elution | 4.13 | 63 | 12224 | 67 | 2.87 | 7.8 |

The load material was clarified cell culture supernatant of a FVII producing CHO cell line supplemented with 2 mM EDTA and pH-adjusted to 6.0. The purification experiment was performed with MES buffers at a pH=6.0 and the elution was induced by chloride counter-ions. FVII:C: FVII chromogenic assay.

TABLE 6

Second Anion Exchange purification a Q-Sepharose Fast Flow (Ca-filtration mode): Yield and impurity balance

| | FVII: Ag | | FVII: C | | CHO HCP | |
|---|---|---|---|---|---|---|
| Step | mg | Yield % | Units | Yield % | mg | reduction |
| Load | 4.13 | — | 12224 | — | 2.87 | — |
| Flow through | 4.75 | >100 | 9686 | 79 | 0.057 | 50 |
| Step 1 + 2 | — | 72 | — | 53 | — | 395 |

The load material was the eluate pool of the first Anion Exchange purification step supplemented with 8 mM calcium and adjusted to pH=>7.6. The purification experiment was performed with Tris buffers at a pH>7.6 and the product was contained in the non-binding fraction.

FVII:C: FVII chromogenic assay.

The invention claimed is:

1. A method for the purification of a divalent cation binding protein comprising the steps of:
    (a) loading a first anion exchange resin material with the divalent cation binding protein in a loading buffer in the absence of divalent cations or at a low concentration thereof;
    (b) eluting the divalent cation binding protein with an eluant comprising a counter-anion to form an eluate containing the divalent cation binding protein;
    (c) supplementing the eluate obtained in step (b) with at least one divalent cation and increasing the pH;
    (d) loading a second anion exchange resin material with the supplemented eluate obtained in step (c); and
    (e) collecting the flow-through from step d) containing the divalent cation binding protein, wherein the divalent cation binding protein is at least 95% w/w pure with respect to host cell protein impurities.

2. The method according to claim 1, wherein in step (c) the pH of the supplemented eluate is increased by at least 0.5 pH units.

3. The method according to claim 1, wherein the eluant in step (b) has a conductivity that is higher than the conductivity of the loading buffer in step (a), and wherein the supplemented eluate in step (c) has a conductivity that is lower than the conductivity of the eluant in step (b).

4. The method according to claim 1, wherein the at least one divalent cation in step (c) is selected from the group consisting of $Ca^{2+}$, $Be^{2+}$, $Ba^{2+}$, $Mg^{2+}$, $Mn^{2+}$, $Sr^{2+}$, $Zn^{2+}$, $Co^{2+}$, $Ni^{2+}$, and $Cu^{2+}$, or combinations thereof.

5. The method according to claim 1, wherein the first and second anion exchange resin materials each have a positively charged group which is independently selected from the group, consisting of diethylaminoethane (DEAE), dimethylaminoethane (DMAE), trimethylaminoethyl (TMAE), polyethyleneimine (PEI), quaternary aminoalkyl, quaternary aminoethane (QAE), and quaternary ammonium (Q).

6. The method according to claim 1, wherein the first and second anion exchange resin materials each carry a primary amine as ligand which is independently selected from the group consisting of aminohexyl, benzamidine, lysine, and arginine.

7. The method according to claim 1, wherein the divalent cation binding protein is a calcium binding protein.

8. The method according to claim 1, wherein the divalent cation binding protein is a vitamin K-dependent protein.

9. The method according to claim 1, wherein the divalent cation binding protein is selected from the group consisting of Factor II, Factor VII, Factor IX, Factor X, Protein C, Protein S, Annexin and calmodulin.

10. The method according to claim 1, wherein the pH of the loading buffer in the loading step (a) is ≤pH 7.4.

11. A method according to claim 1, wherein the method further comprises a step of washing the loaded anion exchange resin material with a washing buffer in the absence of divalent cations after the loading step (a).

12. A method according to claim 11, wherein the eluant in step (b) has a conductivity that is higher than the conductivity of the washing buffer used after the loading step (a).

13. A method according to claim 11, wherein the washing buffer has a pH≤pH 7.4.

14. The method according to claim 11, wherein the pH of the washing buffer is in a range selected from the group consisting of: between pH 5.5 and pH 7.0, between pH 6.0 and pH 7.0, and between pH 6.5 and pH 7.0.

15. The method according to claim 1, wherein the divalent cation binding protein is selected from the group consisting of Factor IX, Factor VII, and Annexin V.

16. The method according to claim 1, wherein the pH of the loading buffer in the loading step (a) is in a range selected from the group consisting of: between pH 5.5 and pH 7.0, between pH 6.0 and pH 7.0, and between pH 6.5 and pH 7.0.

17. The method according to claim 1, wherein the second anion exchange reaction results in a CHO reduction factor of >27.

* * * * *